(12) United States Patent
Powell et al.

(10) Patent No.: US 7,989,659 B2
(45) Date of Patent: Aug. 2, 2011

(54) METHOD AND APPARATUS FOR MAKING ACETIC ACID WITH IMPROVED LIGHT ENDS COLUMN PRODUCTIVITY

(75) Inventors: Nathan Kirk Powell, Waxahachie, TX (US); Nathan Jeremy Nagel, Houston, TX (US); Fred Ronald Olsson, Corpus Christi, TX (US); Wayne David Picard, Houston, TX (US); Ronald David Shaver, Houston, TX (US); Ismael Torres Tejeda, Seabrook, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 11/804,250

(22) Filed: May 17, 2007

(65) Prior Publication Data

US 2008/0287706 A1    Nov. 20, 2008

(51) Int. Cl.
*C07C 51/10*    (2006.01)
*B01D 15/00*    (2006.01)

(52) U.S. Cl. .................................. 562/519; 562/517
(58) Field of Classification Search ................ None
See application file for complete search history.

(56) References Cited

U.S. PATENT DOCUMENTS

| | | | | |
|---|---|---|---|---|
| 4,102,922 | A * | 7/1978 | Price | 562/519 |
| 5,371,286 | A * | 12/1994 | Blay et al. | 562/519 |
| 6,140,535 | A * | 10/2000 | Williams | 562/519 |
| 6,143,930 | A * | 11/2000 | Singh et al. | 562/608 |
| 6,255,527 | B1 * | 7/2001 | Muskett | 562/519 |
| 6,339,171 | B1 * | 1/2002 | Singh et al. | 562/519 |
| 6,642,413 | B2 * | 11/2003 | Thiebaut | 562/517 |
| 6,657,078 | B2 * | 12/2003 | Scates et al. | 562/519 |
| 7,115,772 | B2 * | 10/2006 | Picard et al. | 560/248 |

* cited by examiner

*Primary Examiner* — Rosalynd Keys

(57) ABSTRACT

An improved apparatus and method of producing acetic acid includes condensing overhead vapor to provide reflux to the light ends column as well as condensing vapor from a central portion of the light ends column to increase capacity. Throughput or load on the light ends column is substantially reduced without compromising product quality.

12 Claims, 2 Drawing Sheets

METHOD AND APPARATUS FOR MAKING ACETIC ACID WITH IMPROVED LIGHT ENDS COLUMN PRODUCTIVITY

TECHNICAL FIELD

The present invention relates generally to an apparatus and method for producing acetic acid wherein additional condensing is used on vapor from a central portion of the distillation zone of a light ends column in order to increase system productivity.

BACKGROUND ART

Carbonylation processes are well known in the art. Of particular commercial significance are processes for the carbonylation of methanol to make acetic acid and processes for the carbonylation of methyl acetate to make acetic anhydride. See Applied Homogeneous Catalyst With Organometallic Compounds, Cornils et al., Ed. (Bench Edition) (Wylie, Weinheim, Federal Republic of Germany 2000), Chapter 2, Parts 2.1.2 and following, pp. 104-137. See, also, U.S. Pat. No. 6,642,413 to Thiebaut, as well as U.S. Pat. No. 6,114,576 to Leet et al.

To make acetic acid, one method of choice involves carbonylating methanol in a homogeneous reaction medium wherein rhodium is utilized as a catalyst. Generally, the reaction medium includes catalyst, water, acetic acid, dissolved carbon monoxide (CO), methanol, methyl acetate (MeAc), hydriodic acid (HI), methyl iodide and optionally one or more promoters and/or stabilizers. Methanol and carbon monoxide are fed to a reactor as feedstocks. A portion of the reaction medium is continuously withdrawn and provided to a flasher where product is flashed off and sent (as vapor) to a purification train. The purification train includes a light ends column which removes "light" or low boiling components as overhead and provides a product stream for further purification. A particularly preferred carbonylation process is taught in U.S. Pat. No. 5,144,068 to Smith et al. In this so called "low water" process, an alcohol such as methanol is reacted with carbon monoxide in a liquid reaction medium containing a rhodium catalyst stabilized with an iodide salt, especially lithium iodide along with methyl iodide and methyl acetate in specified proportions. With a finite concentration of water in the reaction medium, the product is the carboxylic acid instead of, for example, the anhydride. The reaction system of the '068 patent not only provides an acid product of unusually low water content at unexpectedly favorable rates, but also exhibits unexpectedly high catalyst stability. That is, the catalyst is resistant to catalyst precipitation out of the reaction medium.

Another method of choice for carbonylating methanol involves utilizing a homogeneous iridium catalyst in the reactor. There is disclosed, for example, in U.S. Pat. No. 5,883,295, to Sunley et al. a process for the production of acetic acid comprising carbonylating with carbon monoxide methanol and/or a reactive derivative thereof, in the substantial absence of a metal promoter and/or ionic iodide co-promoter in a carbonylation reactor containing a liquid reaction composition with an iridium carbonylation catalyst, methyl iodide co-catalyst, water, acetic acid, and methyl acetate wherein there is maintained in the liquid reaction composition: (a) water at a concentration of less than 5% by weight; (b) methyl iodide in a concentration of greater than 12% by weight and (c) in the carbonylation reactor a total pressure of less than 50 bar. See, also, U.S. Pat. No. 5,877,348 to Ditzel et al. and U.S. Pat. No. 5,887,347 also to Ditzel et al.

A frequent production limitation in the purification section of an acetic acid unit is the light ends column. In a typical acetic acid methanol carbonylation process, hot high pressure liquid from the reactor is reduced in pressure across a valve and flashed in a lower pressure flasher vessel. The vapors liberated from this step are fed near the bottom of a light ends (LE) tower. Condensed liquids rich in acetic acid are removed from a liquid sidedraw above the feed and fed forward for further purification, while vapors exiting the tower overhead are condensed and fed to a liquid-liquid decanter. The light phase from the decanter is refluxed to the tower and the heavy phase is recycled to the reactor feed. Thus, the light ends column receives a hot vapor product stream from the flasher and operates to remove most of the methyl acetate and methyl iodide from the stream before the product stream is fed forward for water removal.

SUMMARY OF INVENTION

In accordance with the present invention, hydraulic load in the light ends tower is reduced by partial condensation of the vapors loading the tower. In a typical embodiment, a partial flow of vapor from the tower just above the liquid sidedraw removal is fed to a heat exchanger and cooled to a temperature of, for example 200° F. Condensed liquid is then fed back to the tower to a point above the liquid sidedraw, or simply combined with the liquid sidedraw stream. Hydraulic load is then reduced in the column above the liquid sidedraw. Simulation indicates the tower can be debottlenecked up to 15% without a significant change in liquid sidedraw composition.

BRIEF DESCRIPTION OF DRAWINGS

The invention is described in detail below with reference to the following drawings wherein like numerals designate similar parts and wherein.

DESCRIPTION OF THE PREFERRED EMBODIMENTS

Figure 1:
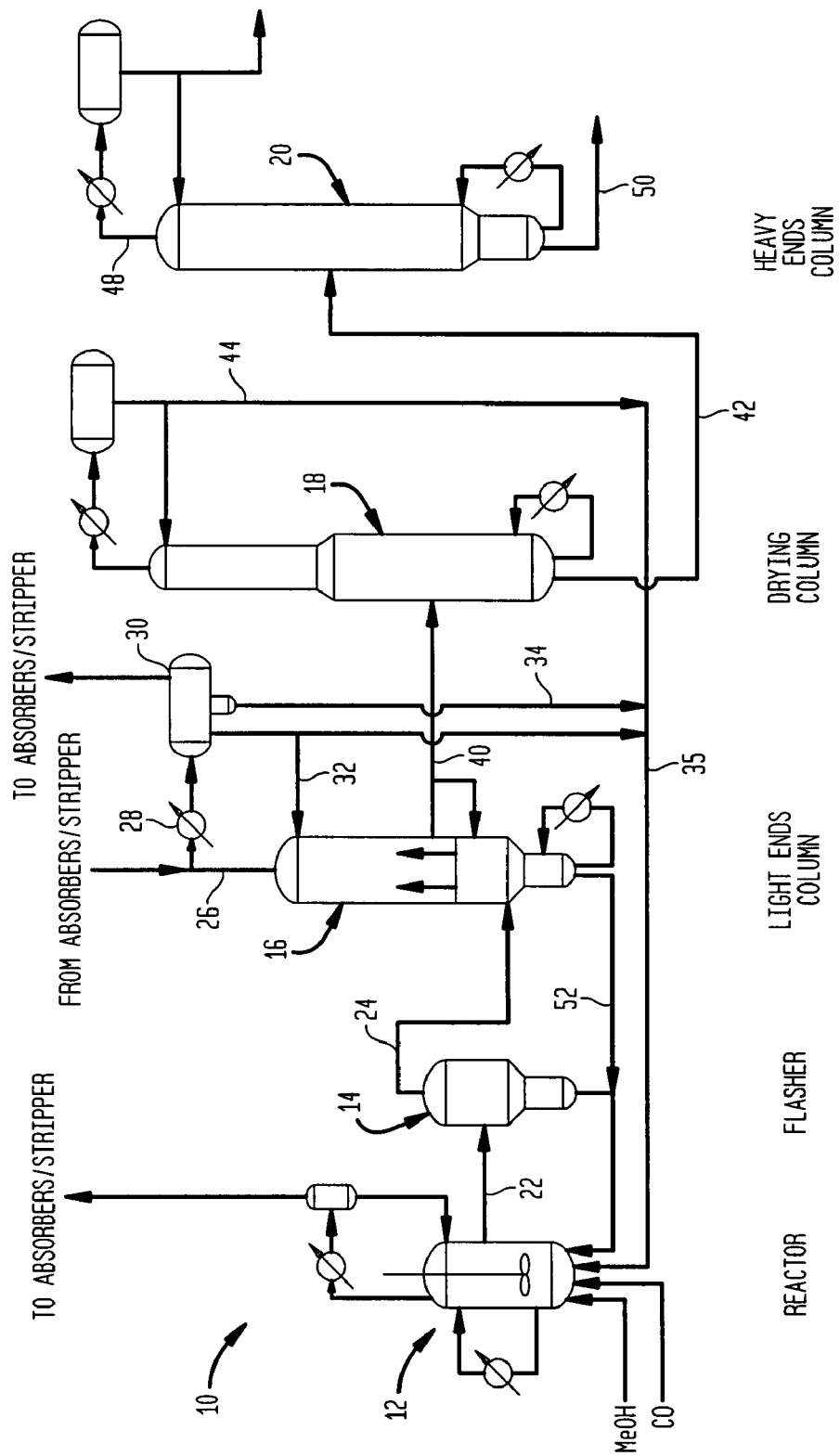
FIG. 1 is a schematic diagram of a conventional methanol carbonylation unit.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppb and like terms refer to weight percent, parts per billion by weight and so forth, unless otherwise indicated.

A "condenser" refers to a heat exchanger configured to remove heat from a vapor in order to condense it to the liquid phase.

The Group VIII catalyst may be a rhodium and/or iridium catalyst. The rhodium metal catalyst may be added in any suitable form such that rhodium is in the catalyst solution as an equilibrium mixture including [Rh(CO)$_2$I$_2$]$^-$ anion as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259 to Smith et al.; 5,026,908 to Smith et al.; and 5,144,068, also to Smith et al., the disclosures of which are hereby incorporated by reference.

Similarly, an iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

An alkyl halide co-catalyst/promoter is generally used in combination with the Group VIII metal catalyst component. Methyl iodide is a preferred as the alkyl halide promoter. Preferably, the concentration of alkyl halide in the liquid reaction composition is in the range 1 to 50% by weight, preferably 2 to 30% by weight.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention includes generally at least a reactive section, and a purification section. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water, and optionally an iodide salt. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed. The crude vapor product stream from the flasher is sent to a purification system which generally includes at least a light ends column and a dehydration column. Carbonylation system may use only 2 purification columns and is preferably operated as described in more detail in U.S. Pat. No. 6,657,078 to Scates et al., entitled "Low Energy Carbonylation Process", the disclosure of which is incorporated herein by reference.

Figure 2:
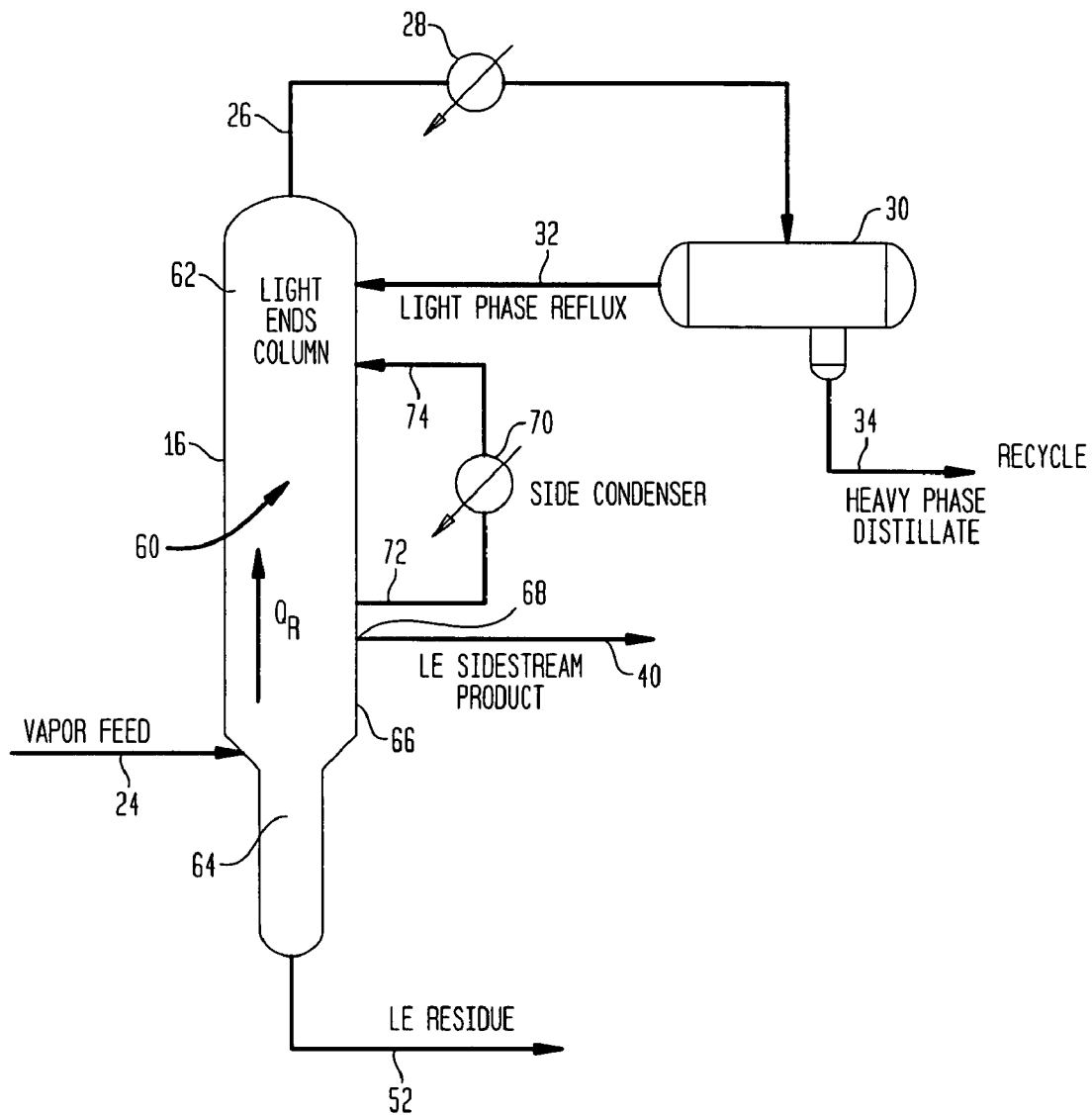
FIG. 2 is a schematic diagram wherein the light ends column of the apparatus of FIG. 1 has been fitted with a side condenser in accordance with the present invention.

Referring to FIGS. 1 and 2, there is shown a carbonylation unit 10 of the class utilized in connection with the present invention. Unit 10 includes a reactor 12, a flasher 14, a light ends column 16, a drying or dehydration column 18 as well as a heavy ends column 20. Reactor 12 includes the reaction medium and there is fed thereto methanol and carbon monoxide. A portion of the reaction medium is continuously provided to flasher 14 via line 22 where crude product is flashed and sent to light ends column 16 via line 24 as a hot vapor feed.

A gaseous purge stream is typically vented from the head of the reactor to prevent buildup of gaseous by-products such as methane, carbon dioxide and hydrogen and to maintain a set carbon monoxide partial pressure at a given total reactor pressure. Optionally (as illustrated in Chinese Patent No. ZL92108244.4), a so-called "converter" reactor can be employed which is located between the reactor and flash vessel 14 shown in FIG. 1. The "converter" produces a vent stream comprising gaseous components which are typically scrubbed with a compatible solvent to recover components such as methyl iodide and methyl acetate. The gaseous purge streams from the reactor and converter can be combined or scrubbed separately and are typically scrubbed with either acetic acid, methanol or mixtures of acetic acid and methanol to prevent loss of low boiling components such as methyl iodide from the process. If methanol is used as the vent scrub liquid solvent, the enriched methanol from the scrubbing system is typically returned to the process by combining with the fresh methanol feeding the carbonylation reactor—although it can also be returned into any of the streams that recycle back to the reactor such as the flasher residue or light ends or dehydration column overhead streams. If acetic acid is used as the vent scrub liquid solvent, the enriched acetic acid from the scrubbing system is typically stripped of absorbed light ends and the resulting lean acetic acid is recycled back to the absorbing step. The light end components stripped from the enriched acetic acid scrubbing solvent can be returned to the main process directly or indirectly in several different locations including the reactor, flasher, or purification columns. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well within the scope of the present invention as will be appreciated from the appended claims and the description which follows.

In column 16, the product is purified of light components which exit the column via line 26, are condensed in a first condenser 28 and then decanted in a decanter 30. The light phase from decanter 30 is refluxed to column 16 via line 32, while the heavy phase from decanter 30 is returned to the reactor via lines 34 and 35. Also provided, but not shown, are absorbers and strippers used to recycle material into the system.

A purified product stream 40 is withdrawn as a (preferably liquid) sidestream from column 16 and fed to drying column 18 where water is removed from the partially purified product. Thereafter, the dried product is provided to heavy ends column 20 via line 42, while the overhead and some product acetic acid is used as reflux for column 18 or recycled to the reactor via lines 35, 44. Product acetic acid is taken overhead from heavy ends column 20 via line 48, while heavy waste is removed via line 50.

Column 16 generates a liquid residue stream 52 which is conventionally recycled with residue from the flasher to the reactor.

Referring more specifically to FIG. 2 there is shown a light ends column defining in its interior a distillation zone 60 having an upper portion 62, a lower portion 64 and a central portion 66 provided with a product sidedraw 68 from which purified product stream 40 is taken. Column 16 includes a second condenser 70 which draws vapor from just above sidedraw 68 via line 72, condenses the vapor and returns the condensed vapor as a liquid to central portion 66 of column 16 via line 74 at a point above the level from which the vapor was taken. The central, upper and lower portions of the distillation zone and the liquid sidedraw have the relative positions shown in FIG. 2.

Column 16 of FIG. 2 is connected as shown in FIG. 1, that is, light ends column 16 is fed at lower portion 64 with hot vapor from flasher 14 via line 24. A purified stream 40 is fed forward to column 18 for water removal and further purification. That is, the improvement of the invention includes generally carbonylating methanol or its reactive derivatives in the presence of water, a catalyst selected from rhodium catalysts, iridium catalysts and mixtures thereof, and a methyl iodide promoter to form an acetic acid reaction mixture in reactor 12 and supplying a stream of the acetic acid reaction mixture to a flasher 14 coupled to the reactor. In flasher 14, the stream of the acetic acid reaction mixture is separated into a liquid recycle stream and a crude product stream including acetic acid, methyl iodide, methyl acetate and water which is fed to light ends column 16 which defines distillation zone 60 including upper portion 62, lower portion 64 and central portion 66 provided with product sidedraw 68. In column 16, the crude product stream is purified in the distillation zone of the light ends column to remove methyl iodide and methyl acetate and generate purified product stream 40, the purified product stream having a lower concentration of methyl iodide and methyl acetate than the crude product stream. Purifying the crude product stream in column 16 includes (i) condensing overhead vapor from the upper portion of the distillation zone of the light ends column with a first condenser 28, (ii) returning at least a portion of the condensed overhead vapor as liquid reflux to the distillation zone of the light ends column via line 32, and (iii) condensing vapor from the central portion of the distillation zone of the light ends column with second condenser 70. A thus purified product stream is taken from sidedraw 68 of the light ends column and fed forward to dehydration column 18 for further purification, including water removal.

Operation of the system of FIG. 1 was simulated with an empirical computer model to illustrate the effects of using a side condenser such as that shown in FIG. 2. Operation of the apparatus at a first production rate (Base Case) was simulated at a first production rate without a side condenser (FIG. 1, unmodified) then with a side condenser (FIG. 2) at the same production rate. The light ends column had a much lower reduced vapor throughput when operated with the side condenser.

Reduced vapor throughput, $Q_R$, is defined as:

$$Q_R = Q_V \sqrt{\frac{\rho_V}{(\rho_L - \rho_V)}}$$

where:
$Q_V$=Volumetric flow rate of vapor to the stage;
$\rho_L$=Mass density of liquid from the stage; and
$\rho_V$=Mass density of vapor to the stage.

Relative values (the ratio of simulated values/simulated values without a side condenser for the same apparatus with substantially the same feed under substantially identical conditions) of the LE column product sidestream mass flow rate and mass flow rate of acetic acid in the LE column product sidestream are given in Table 1 along with calculated values of the methyl iodide and methyl acetate content in the purified product stream as well as the mass flow ratio of liquid condensed in the side condenser/LE product sidestream for the apparatus of FIG. 2.

TABLE 1

Comparison of LE Column Loading With and Without Side Condenser

|  | Without Side Condenser | With Side Condenser |
|---|---|---|
| Relative Mass Flow lbs/hr of LE Product Sidestream | 1 | 1 |
| Relative Mass Flow Rate of Acetic Acid in LE Sidestream | 1 | 1 |
| Relative Reduced Vapor Throughput, $Q_R$ Above Sidedraw | 1 | 0.825 |
| Flow Ratio of Liquid Return from Side Condenser/LE Product Sidestream | — | 0.3 |
| Methyl Acetate Concentration In LE Product Stream (wt. %) | 2.3 | 2.3 |
| Methyl Iodide Concentration In LE Product Stream (wt. %) | 2.7 | 2.7 |

It is seen in Table 1 that at a given production rate, that Reduced vapor throughput, $Q_R$ above the sidedraw was reduced significantly, adding additional capacity, while product purity was substantially identical.

The method and apparatus of the invention may be employed over a range of operating conditions. For example, when the purified product stream is drawn from the light ends column at a mass flow rate, R, vapor from the central portion of the light ends column may be condensed at a rate of from about 0.05R to about 0.5R. Condensation rates in the second condenser of at least about 0.1R, 0.2R and 0.3R are preferred in many cases. The light ends column has a relative reduced vapor throughput, $Q_R$, of from about 0.75 times to about 0.95 times that of a substantially identical column operated under substantially identical conditions without a second condenser. Preferably, the light ends column has a relative reduced vapor throughput, $Q_R$, of less than about 0.9 times that of a substantially identical column operated under substantially identical conditions with a second condenser. The second condenser may be a side condenser external to the light ends column shown in FIG. 2 or the second condenser is internal to the light ends column. In a preferred embodiment, the vapor condensed by the second condenser is from the distillation zone of the light ends column at a level just above the level of the product sidedraw and the vapor condensed by the second condenser is returned to the distillation zone of the light ends column as liquid. Alternatively, vapor condensed by the second condenser is combined with the purified product stream and fed forward for further purification to dehydration column 18.

Generally, the purified product stream has concentrations of methyl iodide and methyl acetate substantially identical to those of a purified product stream drawn from a substantially identical light ends column without a second condenser operated under substantially identical conditions such that product quality is preserved.

The invention has been described in detail and illustrated in connection with numerous embodiments. Modifications to specific embodiments within the spirit and scope of the present invention will be readily apparent to those of skill in the art. Such modifications are within the spirit and scope of the present invention which is set forth in the appended claims.

What is claimed is:

1. A carbonylation process for producing acetic acid comprising:
   (a) carbonylating methanol or its reactive derivatives in the presence of water, a catalyst selected from rhodium catalysts, iridium catalysts and mixtures thereof, and a methyl iodide promoter to form an acetic acid reaction mixture in a reactor;
   (b) separating the stream of the acetic acid reaction mixture into is liquid recycle stream and a crude product stream including acetic acid, methyl iodide, methyl acetate and water;
   (c) feeding the crude product stream to a light ends column having a distillation zone including an upper portion, a lower portion and a central portion provided with a product sidedraw, wherein the crude product stream is fed to the light ends column as a hot vapor at the lower portion thereof;
   (d) purifying the crude product stream in the distillation zone of the light ends column to remove methyl iodide and methyl acetate and generate a purified product stream, the purified product stream having a lower concentration of methyl iodide and methyl acetate than the crude product stream, and wherein the step of purifying the crude product stream includes (i) condensing overhead vapor from the upper portion of the distillation one of the light ends column, (ii) returning at least a portion of the condensed overhead vapor as liquid reflux to the distillation zone of the light ends column, and (iii) condensing vapor from the central portion of the distillation zone of the light ends column at a level above the level of the product sidedraw in a second condenser, and feeding the condensed liquid back into the light ends column at a point above the liquid sidedraw such that the hydraulic load on the light ends column is reduced in the column above the liquid sidedraw as compared to a substantially identical light ends column without a second condenser operated under substantially identical conditions; and
   (e) drawing a purified product stream from the sidedraw of the light ends column,
   wherein the purified product stream is drawn from the light ends column at a mass flow rate, R, and vapor from the central portion of the light ends column is condensed in the second condenser at a rate of 0.05R to 0.5R, and wherein the purity of the purified product stream produced using the light ends column having the second condenser at the reduced hydraulic load on the hot ends column is substantially identical to the purity of a purified product stream produced using a substantially identical light ends column without said second condenser when operated under substantially identical conditions.

2. The process according to claim 1, further comprising feeding the purified product stream forward for further purification, including water removal.

3. The method according to claim 1, wherein the purified product stream is drawn from the light ends column at a mass flow rate, R, and vapor from the central portion of the light ends column is condensed at a rate of at least 0.1R.

4. The method according to claim 1, wherein the purified product stream is drawn from the light ends column at a mass flow rate, R, and vapor from the central portion of the light ends column is condensed at a rate of at least 0.2R.

5. The method according to claim 1, wherein the purified product stream is drawn from the light ends column at a mass flow rate, R, and vapor from the central portion of the light ends column is condensed at a rate of at least 0.3R.

6. A carbonylation process for producing acetic acid comprising:

carbonylating methanol or its reactive derivatives in the presence of water, a catalyst selected from rhodium catalysts, iridium catalysts and mixtures thereof, and a methyl iodide promoter to form an acetic acid reaction mixture in a reactor;

separating the stream of the acetic acid reaction mixture into a liquid recycle stream and a crude product stream including acetic, acid, methyl iodide, methyl acetate and water;

feeding the crude product stream to a light ends column having a distillation zone including an upper portion, a lower portion and a central portion provided with a product sidedraw, wherein the crude product stream is fed to the light ends column as a hot vapor at the lower portion thereof;

purifying the crude product stream in the distillation zone of the light ends column to remove methyl iodide and methyl acetate and generate a purified product stream, the purified product stream having a lower concentration of methyl iodide and methyl acetate than the crude product stream, and wherein the step of purifying the crude product stream includes (i) condensing overhead vapor from the upper portion of the distillation zone of the light ends column with a first condenser, (ii) returning at least a portion of the condensed overhead vapor as liquid reflux to the distillation zone of the light ends column, and (iii) condensing vapor from the central portion of the distillation zone of the light ends column with a second condenser at a level above the level of the product sidedraw, and combining the vapor condensed by the second condenser with the purified product stream and feeding the combined purified product stream forward for further purification such that the hydraulic load on the light ends column is reduced in the column above the liquid sidedraw as compared to a substantially identical light ends column without a second condenser operated under substantially identical conditions; and drawing a purified product stream from the sidedraw of the light ends column, wherein the purified product stream is drawn from the light ends column at as mass how rate, R, and vapor from the central portion of the light ends column is condensed in the second condenser at a rate of 0.05R to 0.5R, and wherein the purity of the purified product stream produced using the light ends column having the second condenser at the reduced hydraulic load on the light ends column is substantially identical to the purity of a purified product stream produced using a substantially identical light ends column without said second condenser when operated under substantially identical conditions.

7. The method according to claim 6, wherein the light ends column has a relative reduced vapor throughput, $Q_R$, of from about 0.75 times to about 0.95 times that of a substantially identical column operated under substantially identical conditions without a second condenser.

8. The method according to claim 6, wherein the light ends column has a relative reduced vapor throughput, $Q_R$, of less than about 0.9 times that of a substantially identical column operated under substantially identical conditions without a second condenser.

9. The method according to claim 6, wherein said second condenser is a side condenser external to the light ends column.

10. The method according to claim 6, wherein the second condenser is internal to the light ends column.

11. The method according to claim 6, wherein vapor condensed by the second condenser is returned to the distillation zone of the light ends column as liquid at a point above the liquid sidedraw.

12. The method according to claim 6, wherein the purified product stream has concentrations of methyl iodide and methyl acetate substantially identical to those of a purified product stream drawn from a substantially identical light ends column without a second condenser operated under substantially identical conditions.

* * * * *